Figure 1:
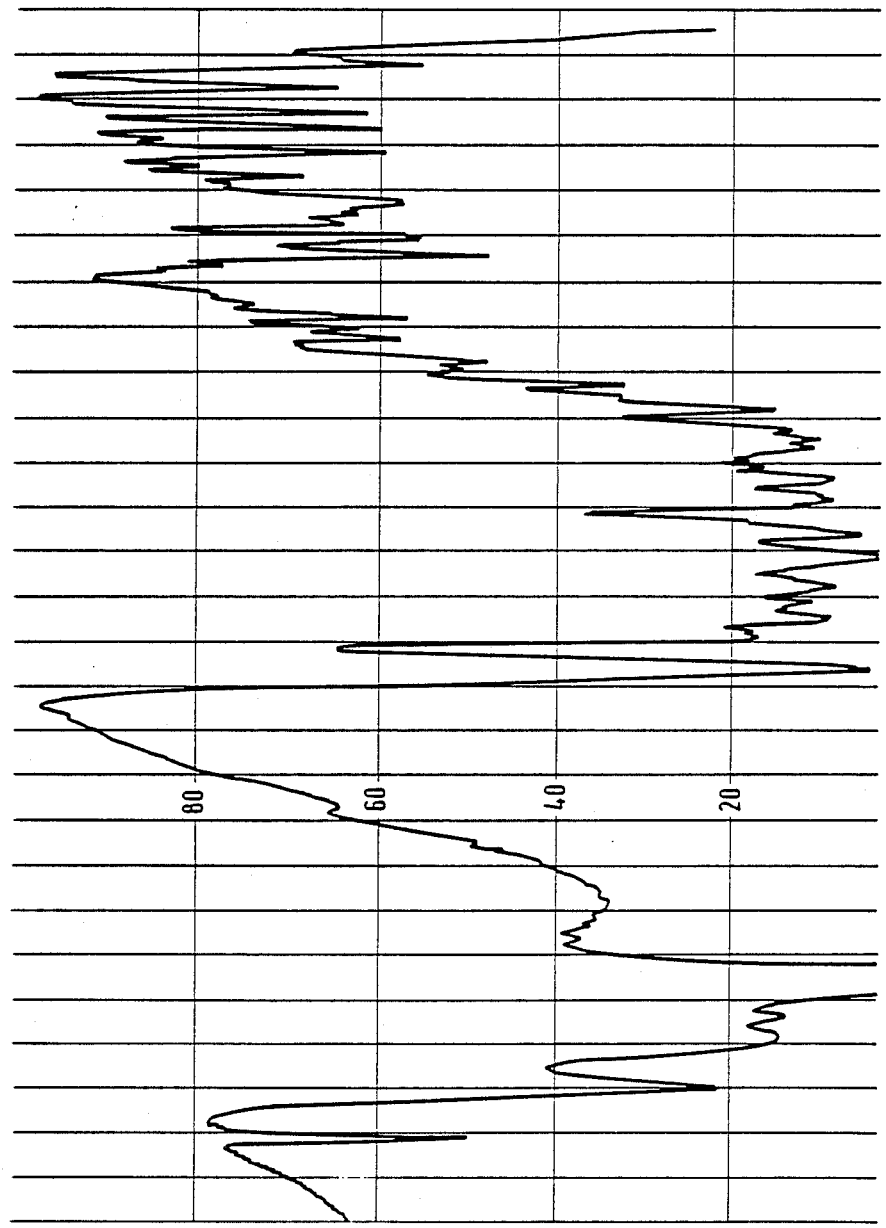

United States Patent [19]

Ward

[11] Patent Number: 4,863,915
[45] Date of Patent: Sep. 5, 1989

[54] β-LACTAM ANTIBIOTICS

[75] Inventor: Neil Ward, Betchworth, England

[73] Assignee: Beecham Group p.l.c., England

[21] Appl. No.: 132,970

[22] PCT Filed: Apr. 10, 1987

[86] PCT No.: PCT/GB87/00246

§ 371 Date: Dec. 10, 1987

§ 102(e) Date: Dec. 10, 1987

[87] PCT Pub. No.: WO87/06231

PCT Pub. Date: Oct. 22, 1987

[30] Foreign Application Priority Data

Apr. 12, 1986 [GB] United Kingdom ............... 8608962

[51] Int. Cl.[4] ................ A61K 31/43; C07D 499/04; C07D 499/48

[52] U.S. Cl. .................................. 514/197; 540/320; 540/331

[58] Field of Search .............. 514/197; 540/320, 331

[56] References Cited

U.S. PATENT DOCUMENTS

| 3,299,046 | 1/1967 | Alburn et al. | 540/320 |
| 3,479,338 | 11/1969 | Adams | 540/321 |
| 3,926,958 | 12/1975 | Callander | 540/321 |
| 4,222,939 | 9/1980 | Clark et al. | 540/320 |

FOREIGN PATENT DOCUMENTS 0131147 1/1985 European Pat. Off. .

OTHER PUBLICATIONS

Chemical Abstracts, vol. 97, No. 17, 144668z, Oct. 1982.

Primary Examiner—Werren B. Lone
Assistant Examiner—Vera C. Clarke
Attorney, Agent, or Firm—Jacobs & Jacobs

[57] ABSTRACT

Crystalline anhydrous amoxycillin is prepared by removing bound solvent molecules from a crystalline solvate (other than the trihydrate) of amoxycillin. A preferred crystalline solvate is the monomethanolate.

10 Claims, 2 Drawing Sheets

β-LACTAM ANTIBIOTICS

This invention relates to β-lactam antibiotics and in particular to crystalline anhydrous amoxycillin, to a process for its preparation from crystalline solvates of amoxycillin, and to pharmaceutically acceptable antibacterial compositions comprising crystalline anhydrous amoxycillin. The invention also relates to novel crystalline solvates of amoxycillin and processes for preparing them.

The crystalline anhydrous amoxycillin of the invention is active against Gram-positive and Gram-negative bacteria and is useful as a therapeutic and prophylactic agent against bacterial infections in animals including man.

6-[D(−)-α-Amino-p-hydroxyphenylacetamido]-penicillanic acid, hereinafter referred to as amoxycillin, is an important penicillin antibiotic which was first disclosed in British Patent Specification No. 1,241,844 and which, as ordinarily prepared, exists as a stable crystalline trihydrate. While the bound water can be removed from the trihydrate by vigorous drying, the resulting material is essentially amorphous and has poor stability.

Despite extensive attempts, including the use of those conditions employed to form the anhydrates of ampicillin, described in, for example, British Patent Specification No. 1,382,409, no crystalline anhydrate of amoxycillin has ever been described. It has been suggested that this is due to steric or structural reasons arising from the structure of amoxycillin itself. For example, Boles et al attributed their failure to crystallize forms of amoxycillin other than the trihydrate at least partly to the fact that stabilization by benzene ring overlap would be reduced in crystalline anhydrous amoxycillin compared to crystalline anhydrous ampicillin, without any corresponding increase in hydrogen bonding, whilst hydrogen bonding in crystalline amoxycillin trihydrate is increased, relative to that in crystalline ampicillin trihydrate, by the presence of the —OH group in the benzene ring ("The Structure of Amoxycillin Trihydrate and a Comparison with the Structures of Ampicillin" Acta Cryst. (1978) B34, 461–466).

European Patent Application Publication No. 0 131 147 describes the preparation of anhydrous crystalline sodium amoxycillin by removing solvent molecules from a solvate (preferably crystalline) of sodium amoxycillin. Solvates of salts of amoxycillin are also known from British Patent Specification No. 1 465 694, which describes a process for the preparation of a crystalline solvate of an alkali metal or alkaline earth metal salt of amoxycillin in which the bound solvent is a pharmaceutically acceptable amide.

No crystalline solvate (other than the trihydrate) of amoxycillin has previously been characterised. However, British Patent Specification No. 1,286,199 describes a process in which amoxycillin trihydrate is treated with a $C_{1-4}$ alkanol such as methanol or ethanol and the resultant gel dried to produce a solid which is stated to be crystalline, is unstable and has a minimum water content of about 3 to 5% w/w. As far as we are aware, no crystalline anhydrous solvate of amoxycillin has previously been described.

It has now been discovered that crystalline anhydrous solvates of amoxycillin (free acid) may be prepared and that subsequent removal of bound solvent gives a stable, anhydrous form (i.e. anhydrate) of amoxycillin having a distinctive infra-red spectrum, and a multiple-line X-ray powder diffractogram characteristic of a crystalline solid.

Accordingly, the present invention provides crystalline anhydrous amoxycillin.

In accordance with a further aspect of the invention there is provided a crystalline solvate (other than the trihydrate) of amoxycillin, more particularly a crystalline anhydrous solvate of amoxycillin.

In accordance with a particular aspect, the invention provides crystalline anhydrous amoxycillin monomethanolate.

The invention also provides a process for the preparation of crystalline, anhydrous amoxycillin, which process comprises removing bound solvent molecules from a crystalline solvate of amoxycillin, which advantageously is crystalline anhydrous amoxycillin monomethanolate.

Advantageously the crystalline solvate of amoxycillin is prepared by bringing together a non-aqueous solution of amoxycillin and a non-aqueous solvent which can form a crystalline solvate with amoxycillin.

Typically, the amoxycillin used as starting material will be the trihydrate.

Preferably, the solvating solvent is labile, i.e. is readily removable from the solvate. Advantageously, the solvating solvent is sufficiently volatile to be removed from the crystalline solvate by heating and/or vacuum drying.

The solvate is isolated in crystalline form by carrying out the precipitation under conditions which allow crystallisation to take place. In one suitable method a solution of amoxycillin is prepared by suspending amoxycillin trihydrate in a suitable solvent or mixture of solvents and adding an organic base such as triethylamine. A suitable solvent system for this stage is dichloromethane or a mixture containing dichloromethane and a solvating solvent. If necessary, a further quantity of the solvating solvent may then be added under conditions which allow crystallisation of the solvate to occur. Normally, crystallisation of the solvate is achieved by addition of a weak acid such as glacial acetic acid.

Preferably a drying agent is added to the solution and the drying agent is removed by filtration before crystallisation of the solvate is induced. Molecular sieves are conveniently used as drying agent in such a process.

A particularly preferred solvating solvent is methanol, with which amoxycillin forms a well defined crystalline solvate, containing approximately 1 mole of methanol per mole of amoxycillin, from which the solvent molecules are readily removed.

In the process for the preparation of the crystalline anhydrous amoxycillin of this invention, the solvent molecules are removed from the crystalline amoxycillin solvate. This removal should be carried out under conditions which do not degrade the penicillin. The method of removal of solvent molecules depends on the nature of the solvate. For example, the solvate-free crystalline anhydrous amoxycillin of the invention may be prepared by conventional drying means, for example by heating, optionally in vacuum. Conveniently the crystalline solvate is exposed to an adsorbate for the solvent molecules, in presence or absence of vacuum, which absorbate may be a conventional drying agent such as phosphorus pentoxide, calcium chloride or silica gel.

The anhydrous amoxycillin formed by the process of this invention is crystalline, usually in the form of prisms or rods. It is also substantially anhydrous, typically containing less than 2%, more especially less than 1%, moisture. For pharmaceutical use, the crystalline anhydrous amoxycillin will contain a pharmaceutically acceptably low level of the solvating solvent, preferably not more than about 0.2% in the case of methanol.

The crystalline anhydrous amoxycillin solvate of the invention is also substantially anhydrous, typically containing less than 2%, more especially less than 1%, moisture.

The infra-red spectrum [Nujol(Trademark) mull] of the crystalline anhydrous amoxycillin of this invention is shown in the accompanying FIG. 1.

Figure 2:
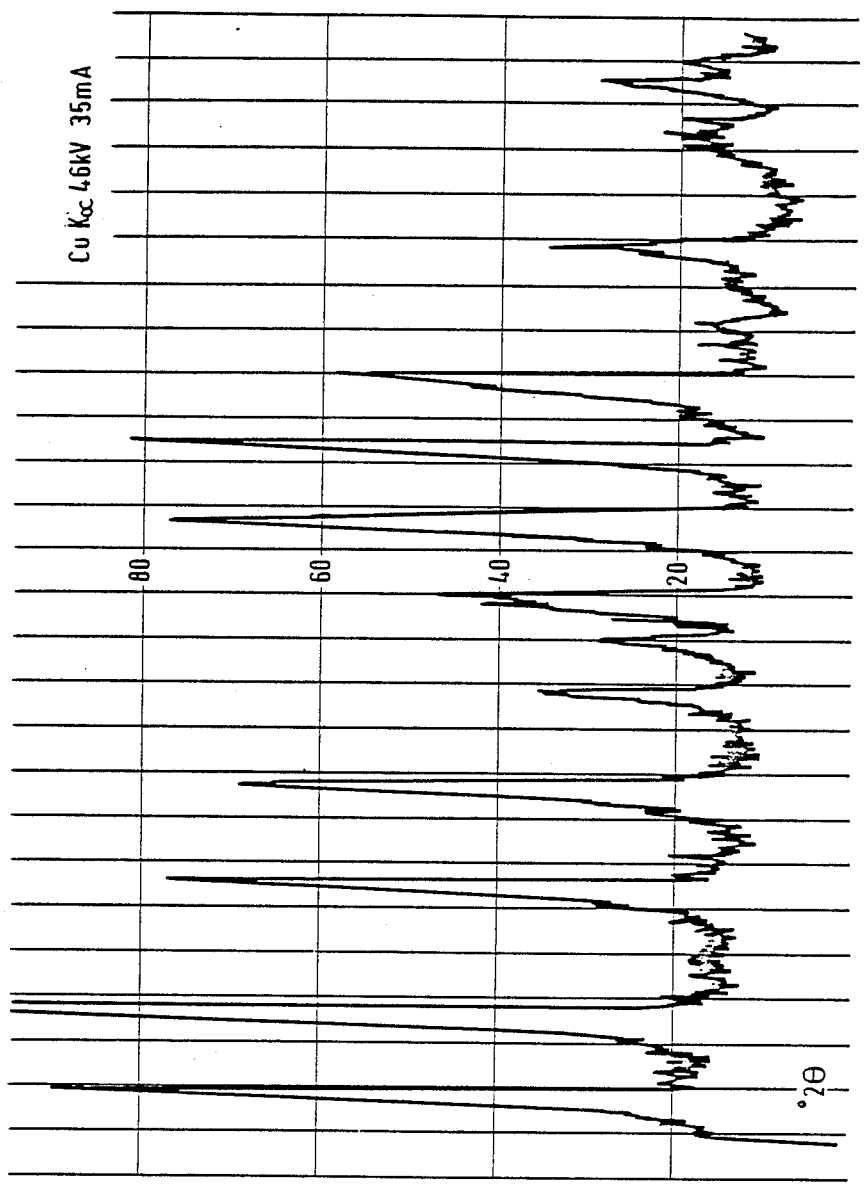

The crystalline anhydrous amoxycillin of this invention is also characterised by an X-ray powder diffractogram, shown in the accompanying FIG. 2, having maxima substantially within $\pm 0.1°$ of the values listed in Example 2 hereinunder.

A further advantage of the process for production of the crystalline anhydrous amoxycillin of the invention is that the process incorporates a step in which amoxycillin is wholly in solution, so that the solution may be sterile filtered. This operation is important for a product which is to be employed for parenteral administration.

The crystalline form of the anhydrous amoxycillin may be reduced or removed without destroying its anhydrous nature, for example by mechanical degradation of the crystals or by dissolving in an anhydrous solvent. Similarly it is possible to retain the crystalline form of the amoxycillin whilst allowing some hydration of the anhydrous state.

In particular, at relative humidities between 11 and 65%, the crystalline anhydrous amoxycillin picks up approximately 4% moisture while retaining its characteristic crystalline form.

The anhydrous amoxycillin may, of course, also be resolvated with, for example, methanol.

The present invention also provides a pharmaceutical composition which comprises crystalline anhydrous amoxycillin and a pharmaceutically acceptable carrier.

The compositions of the invention include those in a form adapted for oral, topical or parenteral use and may be used for the treatment of infections in mammals including humans.

An advantage of the crystalline anhydrous amoxycillin of the invention is that it is hygroscopic and is thus of use in moisture sensitive formulations such as oral formulations where it is not convenient to provide a dessicant.

Thus, the compositions of the invention include in particular those containing, in addition to crystalline anhydrous amoxycillin, one or more further active ingredients, which are water sensitive.

Tablets and capsules for administration may be in unit dose presentation form, and may contain conventional excipients such as binding agents, for example syrup, acacia, gelatin, sorbitol, tragacanth, or polyvinylpyrrolidone: fillers, for example lactose, sugar, maize-starch, calcium phosphate, sorbitol or glycine, tabletting lubricants, for example magnesium stearate, talc, polyethylene glycol or silica; disintegrants, for example potato starch or sodium starch glycollate; or acceptable wetting agents such as sodium lauryl sulphate. The tablets may be coated according to methods well known in normal pharmaceutical practice. Oral liquid preparations may be in the form of a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example fractionated coconut oil, preservatives, for example methyl or propyl p-hydroxybenzoate or sorbic acid, and, if desired, conventional flavouring or colouring agents.

For parenteral administration, fluid unit dosage forms are prepared utilizing the compound and a sterile vehicle, such as water. The compound, depending on the vehicle and concentration used, can be either suspended or dissolved in the vehicle. The vehicle may contain a local anaesthetic such as benzyl alcohol.

Typically the dry powder is sealed in a vial and an accompanying vial of water for injection may be supplied to reconstitute the product prior to use. Advantageously, a surfactant or wetting agent is included in the composition to facilitate uniform distribution of the compound in the aqueous suspension.

The compositions may contain from 0.1-100% by weight, for example from 10-100% by weight or from 10-60% by weight, of the active material, depending on the method of administration. Where the composition comprises dosage units, each unit will preferably contain from 50-3000 mg (eg from 50-500 mg) of the active ingredient. The dosage as employed for adult human treatment will preferably range from 100 to 6000 mg per day, for instance 1500 mg per day depending on the route and frequency of administration. Such a dosage corresponds to 1.5 to 50 mg/kg per day. Suitably the dosage is from 5 to 20 mg/kg per day.

The crystalline anhydrous amoxycillin may be the sole therapeutic agent in the compositions of the invention or a combination with other antibiotics or with a $\beta$-lactamase inhibitor may be employed.

Advantageously, the compositions also comprise a $\beta$-lactamase inhibitor of formula (I) or a pharmaceutically acceptable salt or ester thereof:

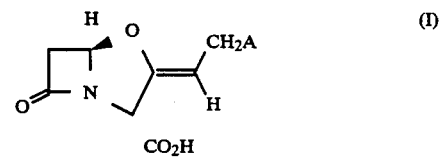

wherein A is hydroxyl, substituted hydroxyl, thiol, substituted thiol, amino, mono- or di-hydrocarbyl-substituted amino, or mono- or di-acylamino, an optionally substituted triazolyl group, or an optionally substituted tetrazolyl group as described in EP 0 053 893.

Preferably A represents hydroxy, i.e. compound (I), preferably in the form of a salt, represents clavulanic acid.

A preferred composition comprises crystalline anhydrous amoxycillin together with a salt of clavulanic acid, in particular the sodium or potassium salt, preferably potassium clavulanate.

A further advantageous composition comprises crystalline anhydrous amoxycillin together with a $\beta$-lactamase inhibitor of formula (II) or a pharmaceutically acceptable salt or in vivo hydrolysable ester thereof:

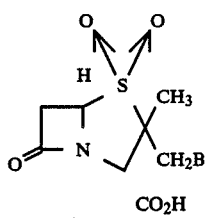

(II)

wherein B represents hydrogen, halogen or a group of formula:

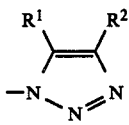

in which $R^1$ and $R^2$ are the same or different and each is hydrogen, $C_{1-6}$ alkoxycarbonyl, or carboxy or a pharmaceutically acceptable salt thereof.

Further suitable β-lactamase inhibitors include 6-alkylidene penems as described in European Patent Application No. 81301683.9 (Publication No. 0 041 768), and European Patent Application No. 85100521.5 (Publication No. 0 154 132) corresponding to laid open published Danish Patent Application No. 324/85.

Further suitable β-lactamase inhibitors include 6β-bromopenicillanic acid and salts and in vivo hydrolysable esters thereof and 6β-iodopenicillanic acid and salts and in vivo hydrolysable esters thereof. Such compositions of this invention comprising a β-lactamase inhibitor are formulated in conventional manner.

The present invention also includes a method of treating bacterial infections in humans and animals which comprises the administration of a therapeutically effective amount of the crystalline anhydrous amoxycillin of the invention.

No toxicological effects are indicated when a compound of the invention is administered in the dosage range described.

The following Examples illustrate the invention.

EXAMPLE 1

Amoxycillin methanolate

Amoxycillin trihydrate (168 g) was suspended in a mixture of methylene chloride (3000 ml) and methanol (300 ml). Triethylamine (168 ml) was added and the mixture stirred thoroughly at room temperature. A clear solution was obtained within 2 minutes.

Molecular sieves type 3A (300 g) were added, the mixture stirred gently for 5 minutes, then filtered through Keiselguhr. The filter bed was washed with 250 ml of 10% methanol in MDC and the combined filtrate and washings treated with glacial acetic acid (72 ml) in one portion with vigorous stirring. Seed crystals of amoxycillin methanolate were added and the mixture allowed to crystallize, with stirring, for 3 hours. Microscopic examination confirmed complete conversion to crystalline material, which showed strong birefringence in polarized light.

The product was collected, washed on the filter with 10% methanol in MDC (750 ml) then thoroughly with MDC and the intermediate amoxycillin methanolate dried briefly in low vacuum.

The mnr spectrum indicated the presence of approximately 1 mole of methanol. The infra-red spectrum (nujol mull) had characteristic bands at 1783 cm$^{-1}$ (β-lactam) and 1031 cm$^{-1}$ (bound methanol). The methanolate gave a sharp x-ray powder diffractogram.

EXAMPLE 2

Amoxycillin anhydrate

Amoxycillin methanolate obtained in Example 1 was heated in a vacuum oven (<0.1 mm Hg) at 60° C. for 19 hours over phosphorous pentoxide. A weight loss of ca. 10% was recorded, and the nmr spectrum confirmed that the methanol had been completely removed. The infra-red spectrum (nujol mull-FIG. 1) had characteristic bands at 3620 cm$^{-1}$ (non-hydrogen bonded OH) and 1761 cm$^{-1}$ (β-lactam). Yield 117 g.

The crystalline anhydrous amoxycillin contained 97.20% amoxycillin free acid, 0.80% water, and less than 0.01% methanol (hplc.).

The x-ray powder diffractogram (FIG. 2) showed a number of strong reflections, notably at the following angles 2θ

| | |
|---|---|
| 7.4 | 14.8 |
| 8.6 | 15.9 |
| 10.5 | 17.1 |
| 11.9 | 18.1 |
| 13.3 | 20.1 |
| 14.1 | |

EXAMPLE 3

Rehydrated amoxycillin anhydrate

Approximately 2 g samples of the anhydrate (obtained in Example 2) were accurately weighed into glass dishes, which were stored open at relative humidities (RH) of 11, 23, 33, 44, 55, 65 and 75% at 20° C. for several weeks. The hygroscopicity was monitored by measuring the weight gain.

The samples of amoxycillin anhydrate were hygroscopic at all the humidities tested. Between 11 and 65% RH the material rapidly picked up moisture until it approximated to about 4% moisture content, after which no further adsorption occurred. At both 55 and 65% RH the resulting materials gave infra-red spectra and X-ray powder diffractograms which were indistinguishable from the starting material.

At 75% RH the material rapidly picked up moisture until it approximated to about 11% moisture content, after which no further moisture pick-up occurred. The resulting material gave an X-ray powder diffractogram which was similar to that of the monomethanolate of Example 1, indicating the formation of a new crystalline phase. The same material was also formed by allowing the monomethanolate of Example 1 to pick up atmospheric moisture.

I claim:

1. Crystalline anhydrous amoxycillin, characterized by an infra red spectrum substantially as shown in FIG. 1 and an X-ray powder diffractogram substantially as shown in FIG. 2.

2. Crystalline anhydrous amoxycillin monomethanolate, characterized by the presence of one mole of methanol per mole of amoxycillin, an infra-red spectrum having bands at 1783 cm$^{-1}$ and 1031 cm$^{-1}$, and a sharp X-ray powder diffractogram.

3. A process for the preparation of the crystalline anhydrous amoxycillin of claim 1, which process comprises removing bound solvent molecules from a crystalline solvate using a non-aqueous solvating solvent.

4. A process according to claim 3, wherein the crystalline solvate is crystalline anhydrous amoxycillin monomethanolate.

5. A process for the preparation of a crystalline solvate of amoxycillin, which process comprises dissolving amoxycillin in a non-aqueous solvent system which optionally includes the solvating solvent, if desired drying the solution, inducing crystallization and recovering the crystalline solvate formed.

6. A process according to claim 5, wherein the non-aqueous solvent is methanol.

7. A pharmaceutical composition useful for treating bacterial infections in humans and animals which comprises an antibacterially effective amount of crystalline anhydrous amoxycillin, characterized by an infra red spectrum substantially as shown in FIG. 1 and an X-ray powder diffractogram substantially as shown in FIG. 2, in combination with a pharmaceutically acceptable carrier.

8. A method of treating bacterial infections in humans and animals which comprises administering to a human or animal in need thereof an antibacterially effective amount of crystalline anhydrous amoxycillin, characterized by an infra red spectrum substantially as shown in FIG. 1 and an X-ray powder diffractogram substantially as shown in FIG. 2, in combination with a pharmaceutically acceptable carrier.

9. A pharmaceutical composition useful for treating bacterial infections in humans and animals which comprises an antibacterially effective amount of crystalline anhydrous amoxycillin, characterized by an infra red spectrum substantially as shown in FIG. 1 and an X-ray powder diffractogram substantially as shown in FIG. 2 and a beta-lactamase inhibitory amount of a beta-lactamase inhibitor, in combination of a pharmaceutically acceptable carrier.

10. A method of treating bacterial infections in humans and animals which comprises administering to a human or animal in need thereof an antibacterially effective amount of crystalline anhydrous amoxycillin, characterized by an infra red spectrum substantially as shown in FIG. 1 and an X-ray powder diffractogram substantially as shown in FIG. 2 and a beta-lactamase inhibitory amount of a beta-lactamase inhibitor, in combination of a pharmaceutically acceptable carrier.

* * * * *